(12) United States Patent
Cheung et al.

(10) Patent No.: US 9,511,359 B2
(45) Date of Patent: Dec. 6, 2016

(54) SELECTIVE HYDROGENATION CATALYST AND METHODS OF MAKING AND USING SAME

(71) Applicant: Chevron Phillips Chemical Company LP, The Woodlands, TX (US)

(72) Inventors: Tin-Tack Peter Cheung, Kingwood, TX (US); Zongxuan Hong, Houston, TX (US); Joseph Bergmeister, III, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/541,672

(22) Filed: Nov. 14, 2014

(65) Prior Publication Data

US 2016/0136630 A1     May 19, 2016

(51) Int. Cl.
*B01J 27/10*     (2006.01)
*B01J 27/12*     (2006.01)
(Continued)

(52) U.S. Cl.
CPC ............ *B01J 31/26* (2013.01); *B01J 21/02* (2013.01); *B01J 21/04* (2013.01); *B01J 23/44* (2013.01);
(Continued)

(58) Field of Classification Search
CPC ............ B01J 23/44; B01J 23/50; B01J 23/58; B01J 23/8926; B01J 23/894; B01J 27/10; B01J 27/12; B01J 27/1806; B01J 27/1817
(Continued)

(56) References Cited

U.S. PATENT DOCUMENTS 4,404,124 A *   9/1983   Johnson .................. B01J 23/50
                                                                                              502/201
4,484,015 A     11/1984   Johnson et al.
(Continued)

FOREIGN PATENT DOCUMENTS

AU     2013201882 A1     4/2013
WO    2010101736 A2     9/2010

OTHER PUBLICATIONS

"Group notation revised in periodic table," Feb. 4, 1985, pp. 26-27, C&EN.
(Continued)

*Primary Examiner* — Patricia L Hailey
(74) *Attorney, Agent, or Firm* — Conley Rose, P.C.; Rodney B. Carroll; Lynda Jolly

(57) ABSTRACT

A method of making a selective hydrogenation catalyst comprising contacting a support with a palladium-containing compound to form a supported-palladium composition; contacting the supported-palladium composition with an organophosphorus compound and a weak acid to form a catalyst composition; and reducing the catalyst composition to form the catalyst. A method of making a selective hydrogenation catalyst comprising contacting an alumina support with a palladium-containing compound to form a supported-palladium composition; contacting the supported-palladium composition with silver nitrate and potassium fluoride to form a mixture; contacting the mixture with an organophosphorus compound and a weak acid to form a catalyst precursor; and reducing the catalyst precursor to form the catalyst.

30 Claims, 2 Drawing Sheets

(51) Int. Cl.
*B01J 31/26* (2006.01)
*B01J 37/28* (2006.01)
*B01J 23/44* (2006.01)
*B01J 31/02* (2006.01)
*B01J 31/04* (2006.01)
*C07C 5/05* (2006.01)
*C07C 5/09* (2006.01)
*B01J 21/02* (2006.01)
*B01J 21/04* (2006.01)
*B01J 23/50* (2006.01)
*B01J 35/00* (2006.01)
*B01J 35/10* (2006.01)
*B01J 37/04* (2006.01)
*B01J 37/16* (2006.01)

(52) U.S. Cl.
CPC ............ *B01J 23/50* (2013.01); *B01J 31/0209* (2013.01); *B01J 31/0262* (2013.01); *B01J 31/0267* (2013.01); *B01J 31/04* (2013.01); *B01J 35/0006* (2013.01); *B01J 35/0093* (2013.01); *B01J 35/1009* (2013.01); *B01J 35/1014* (2013.01); *B01J 37/04* (2013.01); *B01J 37/16* (2013.01); *B01J 37/28* (2013.01); *C07C 5/05* (2013.01); *C07C 5/09* (2013.01); *B01J 2231/645* (2013.01); *B01J 2531/002* (2013.01); *B01J 2531/008* (2013.01)

(58) Field of Classification Search
USPC ................................. 502/162, 208, 216, 224
See application file for complete search history.

(56) References Cited

U.S. PATENT DOCUMENTS

| | | | | |
|---|---|---|---|---|
| 5,475,173 | A * | 12/1995 | Cheung | B01J 23/66 585/258 |
| 7,247,760 | B2 * | 7/2007 | Cheung | B01J 23/44 502/162 |
| 7,541,309 | B2 * | 6/2009 | Trevino | B01J 23/40 208/133 |
| 8,633,127 | B2 * | 1/2014 | Cheung | B01J 23/44 502/162 |
| 9,221,727 | B2 * | 12/2015 | Cheung | C07C 5/09 |
| 2009/0318738 | A1 | 12/2009 | Fecant et al. | |
| 2010/0041929 | A1 | 2/2010 | Bedard et al. | |
| 2010/0217052 | A1 | 8/2010 | Ungar et al. | |
| 2010/0228065 | A1 | 9/2010 | Cheung et al. | |
| 2012/0330067 | A1 * | 12/2012 | Devon | B01J 21/066 568/678 |

OTHER PUBLICATIONS

UOP Method 578-02, "Automated Pore Volume and Pore Size Distribution of Porous Substances by Mercury Porosimetry," 1984, pp. 1-14, UOP LLC.
Foreign communication from a related counterpart application—International Search Report and Written Opinion, PCT/US2015/060128, Feb. 4, 2016, 10 pages.

\* cited by examiner

SELECTIVE HYDROGENATION CATALYST AND METHODS OF MAKING AND USING SAME

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

The present disclosure relates to the production of unsaturated hydrocarbons, and more particularly to a selective hydrogenation catalyst and methods of making and using same.

Background

Unsaturated hydrocarbons such as ethylene and propylene are often employed as feedstocks in preparing value-added chemicals and polymers. Unsaturated hydrocarbons can be produced by pyrolysis or steam cracking of hydrocarbons including hydrocarbons derived from coal, hydrocarbons derived from synthetic crude, naphthas, refinery gases, ethane, propane, butane, and the like. Unsaturated hydrocarbons produced in these manners usually contain small proportions of highly unsaturated hydrocarbons such as acetylenes and diolefins that adversely affect the production of subsequent chemicals and polymers. Thus, to form an unsaturated hydrocarbon product such as a polymer grade monoolefin, the amount of acetylenes and diolefins in the monoolefin stream is typically reduced. For example, in polymer grade ethylene, the acetylene content typically is less than about 2 ppmw.

One technique commonly used to reduce the amount of acetylenes and diolefins in an unsaturated hydrocarbon stream primarily comprising monoolefins involves selectively hydrogenating the acetylenes and diolefins to monoolefins. This process is selective in that hydrogenation of the monoolefin and the highly unsaturated hydrocarbons to saturated hydrocarbons is minimized. For example, the hydrogenation of ethylene or acetylene to ethane is minimized.

One challenge to the selective hydrogenation process is the reduction in catalyst activity over time. Typically, catalyst deactivation can be attributed to the presence of poisons, such as sulfur, in the feedstock that result in a reduction in the number of active catalytic sites. Therefore, a need exists for a selective hydrogenation catalyst that displays an improved recovery from a sulfur-poisoning event.

SUMMARY

Disclosed herein is a method of making a selective hydrogenation catalyst comprising contacting a support with a palladium-containing compound to form a supported-palladium composition; contacting the supported-palladium composition with an organophosphorus compound and a weak acid to form a catalyst composition; and reducing the catalyst composition to form the catalyst.

Also disclosed herein is a method of making a selective hydrogenation catalyst comprising contacting a support with a palladium-containing compound to form a supported-palladium composition; contacting the supported-palladium composition with silver nitrate and potassium fluoride to form a mixture; contacting the mixture with an organophosphorus compound and a weak acid to form a catalyst precursor; and reducing the catalyst precursor to form the catalyst.

Also disclosed herein is a composition comprising (i) a supported hydrogenation catalyst comprising palladium, a weak acid and a support, wherein the supported hydrogenation catalyst is capable of selectively hydrogenating highly unsaturated hydrocarbons to unsaturated hydrocarbons, the support has a surface area of from about 2 $m^2/g$ to about 100 $m^2/g$, and greater than about 90 wt. % of the palladium is concentrated near a periphery of the support; and (ii) an organophosphorus compound.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
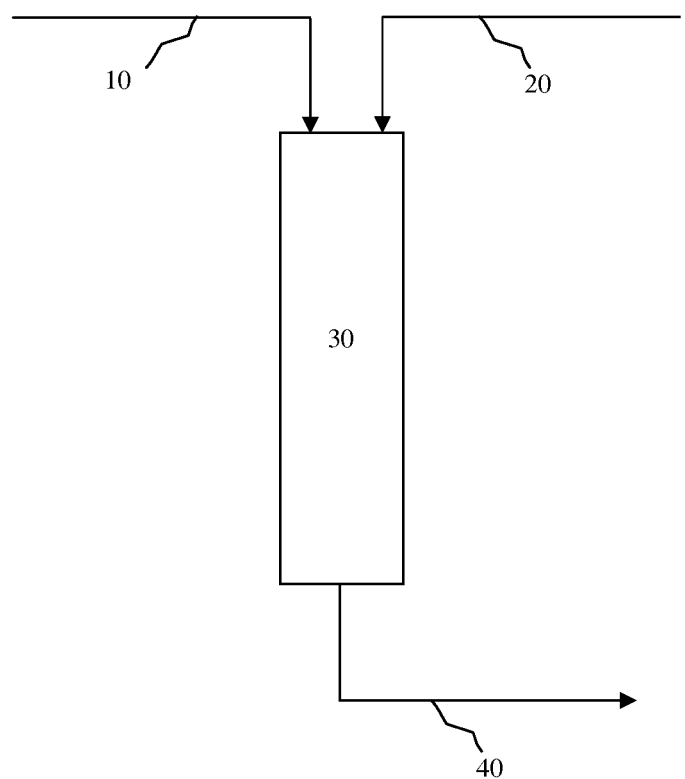
FIG. 1 depicts a process flow diagram of an embodiment of a selective hydrogenation process.

It should be understood at the outset that although an illustrative implementation of one or more embodiments are provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

In an embodiment, a method of making a selective hydrogenation catalyst comprises contacting an inorganic catalyst support with a palladium-containing compound to form a supported-palladium composition and contacting the supported-palladium composition with an organophosphorus compound and a weak acid. Herein, the disclosure will focus on the use of phosphine oxides, phosphates, phosphinates, phosphonates, or combinations thereof as the organophosphorus compound, although phosphines, phosphites, phosphinites, phosphonites, or combinations thereof are also contemplated organophosphorus compound precursors suitable for use in this disclosure and will be described in more detail later herein. In an embodiment, the methodologies disclosed herein result in selective hydrogenation catalysts having enhanced selectivity and an improved recovery from deactivation by sulfur. Catalysts of the type disclosed herein can be utilized as selective hydrogenation catalysts (SHC).

It is to be understood that the SHC is the result of contacting the components disclosed herein (e.g., inorganic support, palladium, organophosphorus compound, weak acid, etc. . . . ) to form a composition that can be utilized as a selective hydrogenation catalyst. The materials as utilized to form the SHC can contact and be converted such that the original material is not discernible as a separate entity in the SHC. For example, the disclosure will describe utilization of a metal-containing compound in the formation of the SHC. The SHC utilized as a selective hydrogenation catalyst can contain one or more components of the metal-containing compound however, the metal-containing compound as originally contacted with the other components of the SHC may not be discernible in the final product.

The SHC can be used for selectively hydrogenating highly unsaturated hydrocarbons to unsaturated hydrocarbons. As used herein, a highly unsaturated hydrocarbon is defined as a hydrocarbon containing a triple bond, two conjugated carbon-carbon double bonds, or two cumulative carbon-carbon double bonds. As used herein, an unsaturated hydrocarbon is defined as a hydrocarbon containing an isolated carbon-carbon double bond. Examples of highly unsaturated hydrocarbons include without limitation acetylene, methylacetylene, and propadiene. Examples of unsaturated hydrocarbons include ethylene and propylene. It is also understood that the term "catalyst" refers to the support together with the materials impregnated in or on the support.

In an embodiment, the SHC can comprise an inorganic support such as for example and without limitation aluminas, silicas, titanias, zirconias, aluminosilicates (e.g., clays, ceramics, and/or zeolites), spinels (e.g., zinc aluminate, zinc titanate, and/or magnesium aluminate), or combinations thereof. In an embodiment, the SHC comprises an alumina support. In some embodiments, the alumina support comprises an alpha (α)-alumina support.

The inorganic support can have a surface area of from about 2 to about 100 square meters per gram ($m^2/g$), alternatively of from about 2 $m^2/g$ to about 75 $m^2/g$, alternatively of from about 3 $m^2/g$ to about 50 $m^2/g$, alternatively of from about 4 $m^2/g$ to about 25 $m^2/g$, or alternatively of from about 5 $m^2/g$ to about 15 $m^2/g$. The surface area of the support can be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is incorporated herein by reference in its entirety.

Particles of the inorganic support generally have an average diameter of from about 1 mm to about 10 mm, alternatively from about 2 mm to about 6 mm, alternatively from about 2 mm to about 4 mm, alternatively from about 3 mm to about 5 mm, alternatively from about 3.8 mm to about 4.2 mm, or alternatively from about 4 mm to about 6 mm and can have any suitable shape. In an embodiment, the shape of the inorganic support can be cylindrical. In an alternative embodiment, the shape of the inorganic support can be spherical. In an embodiment, the inorganic support can be present in an amount such that it comprises the balance of the SHC when all other components are accounted for.

In an embodiment, the SHC comprises a Group 10 metal. Groups of elements of the table are indicated using the numbering scheme indicated in the version of the periodic table of elements published in *Chemical and Engineering News*, 63(5), 27, 1985. In an embodiment, the metals can comprise nickel, palladium, platinum, or combinations thereof. In an embodiment, the metal comprises palladium. Palladium can be added to the SHC by contacting the inorganic support with a palladium-containing compound to form a supported-palladium composition as will be described in more detail later herein. Examples of suitable palladium-containing compounds include without limitation palladium chloride, palladium nitrate, ammonium hexachloropalladate, ammonium tetrachloropalladate, palladium acetate, palladium bromide, palladium iodide, tetraamminepalladium nitrate, or combinations thereof. In an embodiment, the palladium-containing compound is a component of an aqueous solution. An example of a palladium-containing solution suitable for use in this disclosure includes without limitation a solution comprising palladium metal.

In an embodiment, the SHC can be prepared using a palladium-containing compound in an amount of from about 0.005 wt. % to about 5 wt. % based on the total weight of the SHC, alternatively from about 0.01 wt. % to about 3 wt. %, alternatively from about 0.02 wt. % to about 1 wt. %, alternatively from about 0.02 wt. % to about 0.04 wt. %, alternatively from about 0.018 wt. % to about 0.05 wt. %, or alternatively from about 0.03 wt. % to about 0.05 wt. %. The amount of palladium incorporated into the SHC can be in the range described herein for the amount of palladium-containing compound used to prepare the SHC.

In an embodiment, the SHC comprises an organophosphorus compound. In an embodiment, the organophosphorus compound can be represented by the general formula $(R)_x(OR')_yP=O$; wherein x and y are integers ranging from 0 to 3 and x plus y equals 3; wherein each R can be hydrogen, a hydrocarbyl group, or combinations thereof; and wherein each R' can be a hydrocarbyl group. In some embodiments, the organophosphorus compound can include compounds such as phosphine oxides, phosphinates, phosphonates, phosphates, or combinations of thereof. For purposes of this application, the term "hydrocarbyl(s)" or "hydrocarbyl group(s)" as used herein in accordance with the definition specified by IUPAC: a univalent group or groups derived by the removal of one hydrogen atom from a carbon atom of a "hydrocarbon." A hydrocarbyl group can be an aliphatic, inclusive of acyclic and cyclic groups. A hydrocarbyl group can include rings, ring systems, aromatic rings, and aromatic ring systems. Hydrocarbyl groups can include, by way of example, aryl, alkyl, cycloalkyl, and combinations of these groups, among others. Hydrocarbyl groups can be linear or branched unless otherwise specified. For the purposes of this application, the terms "alkyl," or "cycloalkyl" refers to a univalent group derived by removal of a hydrogen atom from any carbon atom of an alkane. For the purposes of this application, the terms "aryl," or "arylene" refers to a univalent group derived by removal of a hydrogen atom from any carbon atom of an aryl ring.

In an embodiment, the hydrocarbyl group can have from about 1 to about 30 carbon atoms, alternatively from about 2 to about 20 carbon atoms, or alternatively from about 3 to about 15 carbon atoms. In other embodiments, the hydrocarbyl group can have from about 4 to about 30 carbon atoms, alternatively from about 4 to about 20 carbon atoms, or alternatively from about 4 to about 15 carbon atoms.

Generally, the alkyl group for any feature which calls for an alkyl group described herein can be a methyl, ethyl, n-propyl(1-propyl), isopropyl (2-propyl), n-butyl(1-butyl), sec-butyl(2-butyl), isobutyl (2-methyl-1-propyl), tert-butyl (2-methyl-2-propyl), n-pentyl(1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), or n-hexyl(1-hexyl) group. In an embodiment, the alkyl group can be a primary, secondary, or tertiary alkyl group.

Organophosphorus compounds described herein are not considered to encompass elemental phosphorus, or inorganic phosphorus compounds, except that which can be produced during the preparation of the SHC described herein. Inorganic phosphorus compounds encompass monobasic, dibasic, and tribasic phosphates such as tribasic potassium phosphate ($K_3PO_4$), tribasic sodium phosphate ($Na_3PO_4$), dibasic potassium phosphate ($K_2HPO_4$), dibasic sodium phosphate ($Na_2HPO_4$), monobasic potassium phosphate ($KH_2PO_4$), and monobasic sodium phosphate ($NaH_2PO_4$). Inorganic phosphorus compounds also encompass the corresponding phosphorus acid of the above-mentioned salts. Inorganic phosphorus compounds also encompass anionic inorganic phosphorus compounds containing pentavalent phosphorus and halogens. Examples of anionic inorganic phosphorus compounds include without limitation sodium and potassium hexafluorophosphate.

An organophosphorus compound suitable for use in this disclosure can be further characterized by a low-boiling point wherein a low boiling point refers to a boiling point of equal to or less than about 100° C. at atmospheric pressure. Alternatively, an organophosphorus compound suitable for use in this disclosure can be further characterized by a high boiling point wherein a high boiling point refers to a boiling point of equal to or greater than about 100° C. at atmospheric pressure.

In an embodiment, the organophosphorus compound comprises a phosphine oxide which can be represented by the general formula $(R)_3P=O$; wherein each R can be hydrogen, a hydrocarbyl group, or combinations thereof. Examples of phosphine oxides suitable for use in this disclosure include without limitation butyldiethylphosphine oxide, butyldimethylphosphine oxide, butyldiphenylphosphine oxide, butyldipropylphosphine oxide, decyldiethylphosphine oxide, decyldimethylphosphine oxide, decyldiphenylphosphine oxide, dibutyl(2-methylphenyl)-phosphine oxide, diethyl(3-methylphenyl)-phosphine oxide, ethyldioctylphosphine oxide, ethyldibutylphosphine oxide, ethyldimethylphosphine oxide, ethyldiphenylphosphine oxide, ethyldipropylphosphine oxide, heptyldibutylphosphine oxide, heptyldiethylphosphine oxide, heptyldimethyl phosphine oxide, heptyldipentylphosphine oxide, heptyldiphenylphosphine oxide, hexyldibutylphosphine oxide, hexyldiethylphosphine oxide, hexyldimethyl phosphine oxide, hexyldipentylphosphine oxide, hexyldiphenylphosphine oxide, methylbis(4-methylphenyl)-phosphine oxide, methyldibutylphosphine oxide, methyldidecylphosphine oxide, methyldiethylphosphine oxide, methyldiphenylphosphine oxide, methyldipropylphosphine oxide, octyldimethylphosphine oxide, octyldiphenylphosphine oxide, pentyldibutylphosphine oxide, pentyldiethylphosphine oxide, pentyldimethylphosphine oxide, pentyldiphenylphosphine oxide, phenyldibutylphosphine oxide, phenyldiethylphosphine oxide, phenyldimethylphosphine oxide, phenyldipropylphosphine oxide, propyldibutylphosphine oxide, propyldimethylphosphine oxide, propyldiphenylphosphine oxide, tris(2,6-dimethylphenyl)-phosphine oxide, tris(2-methylphenyl)-phosphine oxide, tris(4-methylphenyl)-phosphine oxide, tris[4-(1,1-dimethylethyl)phenyl]-phosphine oxide, (1-methylethyl)diphenyl-phosphine oxide, 4-(diphenylmethyl)phenyl]diphenyl-phosphine oxide, bis(2-methylphenyl)(2-methylpropyl)-phosphine oxide, or combinations thereof. In some embodiments, phosphine oxides suitable for use in this disclosure include without limitation tributylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, or combinations thereof.

In an embodiment, the organophosphorus compound comprises an organic phosphate which can be represented by the general formula $(OR')_3P=O$; wherein each R' can be a hydrocarbyl group. Examples of phosphates suitable for use in this disclosure include without limitation (1-methylethyl)diphenyl phosphate, 2-ethylphenyldiphenyl phosphate, 4-(diphenylmethyl)phenyl]diphenyl phosphate, bis(2-methylphenyl)(2-methylpropyl)phosphate, butyldiethylphosphate, butyldimethylphosphate, butyldiphenylphosphate, butyldipropylphosphate, crecyldiphenylphosphate, decyldiethylphosphate, decyldimethylphosphate, decyldiphenylphosphate, dibutyl(2-methylphenyl)phosphate, diethyl(3-methylphenyl)phosphate, ethyldibutylphosphate, ethyldimethylphosphate, ethyldioctylphosphate, ethyldiphenylphosphate, ethyldipropylphosphate, heptyldibutylphosphate, heptyldiethylphosphate, heptyldimethyl phosphate, heptyldipentylphosphate, heptyldiphenylphosphate, hexyldibutylphosphate, hexyldiethylphosphate, hexyldimethyl phosphate, hexyldipentylphosphate, hexyldiphenylphosphate, methylbis(4-methylphenyl)phosphate, methyldibutylphosphate, methyldidecylphosphate, methyldiethylphosphate, methyldiphenylphosphate, methyldipropylphosphate, octyldimethylphosphate, octyldiphenylphosphate, pentyldibutylphosphate, pentyldiethylphosphate, pentyldimethylphosphate, pentyldiphenylphosphate, phenyldibutylphosphate, phenyldiethylphosphate, phenyldimethylphosphate, phenyldipropylphosphate, propyldibutylphosphate, propyldimethylphosphate, propyldiphenylphosphate, tri(2,3-dichloropropyl)phosphate, tri(2,6-dimethylphenyl)phosphate, tri(2-chloroethyl)phosphate, tri(nonylphenyl)phosphate, tris(2,6-dimethylphenyl)phosphate, tris(2-methylphenyl)phosphate, tris(4-methylphenyl)phosphate, tris[4-(1,1-dimethylethyl)phenyl]phosphate, or combinations thereof. In some embodiments, phosphates suitable for use in this disclosure include tributylphosphate, tricresyl phosphate, tricyclohexyl phosphate, tridecylphosphate, triethylphosphate, triheptylphosphate, triisopropyl phosphate, trimethylphosphate, trioctadecyl phosphate, trioctylphosphate, tripentylphosphate, triphenylphosphate, tripropylphosphate, trixylylphosphate, or combinations thereof.

In an embodiment, the organophosphorus compound comprises a phosphinate, which can be represented by the general formula $(R)_2(OR')P=O$; wherein each R can be hydrogen, a hydrocarbyl group, or combinations thereof; and wherein each R' can be a hydrocarbyl group. Examples of phosphinates suitable for use in this disclosure include without limitation butyl butylphosphinate, butyl dibutylphosphinate, butyl diethylphosphinate, butyl diphenylphosphinate, butyl dipropylphosphinate, butyl ethylphosphinate, butyl heptylphosphinate, butyl hexylphosphinate, butyl pentylphosphinate, butyl phenylphosphinate, butyl propylphosphinate, decyl pentylphosphinate, butyl butylpentylphosphinate, ethyl butylphosphinate, ethyl decylphosphinate, ethyl dibutylphosphinate, ethyl diethylphosphinate, ethyl dimethylphosphinate, ethyl diphenylphosphinate, ethyl dipropylphosphinate, ethyl ethylphosphinate, ethyl heptylphosphinate, ethyl hexylphosphinate, ethyl octylphosphinate, ethyl pentylphosphinate, ethyl phenylphosphinate, ethyl propylphosphinate, heptyl dibutylphosphinates, heptyl pentylphosphinate, heptylphosphinate, hexyl dibutylphosphinate, hexyl pentylphosphinate, isopropyl diphenylphosphinate, methyl butylphosphinate, methyl decylphosphinate, methyl dibutylphosphinate, methyl diethylphosphinate, methyl dimethylphosphinate, methyl diphenylphosphinates, methyl dipropylphosphinate, methyl ethylphosphinate, methyl heptylphosphinate, methyl hexylphosphinate, methyl octylphosphinate, methyl pentylphosphinate, methyl phenylphosphinate, methyl propylphosphinate, octyl pentylphosphinate, octylphosphinate, pentyl dibutylphosphinate, pentylphosphinate, phenyl butylphosphinate, phenyl decylphosphinate, phenyl dibutylphosphinate, phenyl diethylphosphinate, phenyl diethylphosphinate, phenyl dimethylphosphinate, phenyl diphenylphosphinate, phenyl diphenylphosphinate, phenyl dipropylphosphinate, phenyl ethylphosphinate, phenyl heptylphosphinate, phenyl hexylphosphinate, phenyl octylphosphinate, phenyl pentylphosphinate, phenyl pentylphosphinate, phenyl phenylphosphinate, phenyl propylphosphinate, phenylphosphinate, propyl diphenylphosphinate, or combinations thereof.

In an embodiment, the organophosphorus compound comprises a phosphonate, which can be represented by the general formula $(R)(OR')_2P=O$; wherein each R can be hydrogen, a hydrocarbyl group, or combinations thereof; and wherein each R' can be a hydrocarbyl group. Examples of phosphonates suitable for use in this disclosure include without limitation (1-methylethyl)diphenyl phosphonate, 2-ethylphenyldiphenyl phosphonate, 4-(diphenylmethyl)phenyl]diphenyl phosphonate, bis(2-methylphenyl) (2-methylpropyl)phosphonate, butyldiethylphosphonate, butyldimethylphosphonate, butyldiphenylphosphonate, butyldipropylphosphonate, crecyldiphenylphosphonate, decyldiethylphosphonate, decyldimethylphosphonate, decyldiphenylphosphonate, dibutyl(2-methylphenyl)phosphonate, diethyl(3-methylphenyl)phosphonate, ethyldibutylphosphonate, ethyldimethylzphosphonate, ethyldioctylphosphonate, ethyldiphenylphosphonate, ethyldipropylphosphonate, heptyldibutylphosphonate, heptyldiethylphosphonate, heptyldimethyl phosphonate, heptyldipentylphosphonate, heptyldiphenylphosphonate, hexyldibutylphosphonate, hexyldiethylphosphonate, hexyldimethyl phosphonate, hexyldipentylphosphonate, hexyldiphenylphosphonate, methylbis(4-methylphenyl)phosphonate, methyldibutylphosphonate, methyldidecylphosphonate, methyldiethylphosphonate, methyldiphenylphosphonate, methyldipropylphosphonate, octyldimethylphosphonate, octyldiphenylphosphonate, pentyldibutylphosphonate, pentyldiethylphosphonate, pentyldimethylphosphonate, pentyldiphenylphosphonate, phenyldibutylphosphonate, phenyldiethylphosphonate, phenyldimethylphosphonate, phenyldipropylphosphonate, propyldibutylphosphonate, propyldimethylphosphonate, propyldiphenylphosphonate, tri(2,3-dichloropropyl)phosphonate, tri(2,6-dimethylphenyl)phosphonate, tri(2-chloroethyl)phosphonate, tri(nonylphenyl-phosphonate, tris(2,6-dimethylphenyl)phosphonate, tris(2-methylphenyl)phosphonate, tris(4-methylphenyl)phosphonate, tris[4-(1,1-dimethylethyl)phenyl]phosphonate, or combinations thereof. In some embodiments, phosphonates suitable for use in this disclosure include without limitation tributylphosphonate, tricresyl phosphonate, tricyclohexyl phosphonate, tridecylphosphonate, triethylphosphonate, triheptylphosphonate, triisopropyl phosphonate, trimethylphosphonate, trioctadecyl phosphonate, trioctylphosphonate, tripentylphosphonate, triphenylphosphonate, tripropylphosphonate, trixylylphosphonate, or combinations thereof.

In an embodiment, the SHC comprises a precursor to the organophosphorus compound. The organophosphorus compound precursor can comprise any material that can be converted to the organophosphorus compound that activates the SHC under the conditions to which the selective hydrogenation catalyst is exposed and that is compatible with the other components of the SHC. In an embodiment, the organophosphorus compound precursor can be represented by the general formula $(R)_x(OR')_yP$; wherein x and y are integers ranging from 0 to 3 and x plus y equals 3; wherein each R can be hydrogen, a hydrocarbyl group, or combinations thereof; and wherein each R' can be a hydrocarbyl group. The organophosphorus compound precursor can include without limitation phosphines, phosphites, phosphinites, phosphonites, or combinations thereof. In an embodiment, the organophosphorus compound precursor comprises a phosphine that can form a phosphine oxide when exposed to an oxidizing agent and/or temperatures greater than about 20° C. In an embodiment, the organophosphorus compound precursor comprises a phosphite that can form a phosphate when exposed to an oxidizing agent and/or temperatures greater than about 20° C. In an embodiment, the organophosphorus compound precursor comprises a phosphinite that can form a phosphinate when exposed to oxidizing agent and/or temperatures greater than about 20° C. In an embodiment, the organophosphorus compound precursor comprises a phosphonite that can form a phosphonate when exposed to air and/or temperatures greater than about 20° C.

In an embodiment, the organophosphorus compound precursor comprises phosphines, which can be represented by the general formula $(R)_3P$; wherein each R can be hydrogen, a hydrocarbyl group, or combinations thereof. Examples of phosphines suitable for use as phosphine oxide precursors in this disclosure include without limitation (1-methylethyl)diphenylphosphine, 2-ethylphenyldiphenyl phosphine, 4-(diphenylmethyl)phenyl]diphenylphosphine, bis(2-methylphenyl) (2-methylpropyl)phosphine, butyldiethylphosphine, butyldimethylphosphine, butyldiphenylphosphine, butyldipropylphosphine, crecyldiphenylphosphine, cyclohexyldiphenylphosphine, decyldiethylphosphine, decyldimethylphosphine, decyldiphenylphosphine, dibutyl(2-methylphenyl)phosphine, dicyclohexylphenylphosphine, diethyl (3-methylphenyl)phosphine, ethyldibutylphosphine, ethyldimethylphosphine, ethyldioctylphosphine, ethyldiphenylphosphine, ethyldipropylphosphine, heptyldibutylphosphine, heptyldiethylphosphine, heptyldimethyl phosphine, heptyldipentylphosphine, heptyldiphenylphosphine, hexyldibutylphosphine, hexyldiethylphosphine, hexyldimethyl phosphine, hexyldipentylphosphine, hexyldiphenylphosphine, methylbis(4-methylphenyl)phosphine, methyldibutylphosphine, methyldidecylphosphine, methyldiethylphosphine, methyldiphenylphosphine, methyldipropylphosphine, octyldimethylphosphine, octyldiphenylphosphine, pentyldibutylphosphine, pentyldiethylphosphine, pentyldimethylphosphine, pentyldiphenylphosphine, phenyldibutylphosphine, phenyldiethylphosphine, phenyldimethylphosphine, phenyldipropylphosphine, propyldibutylphosphine, propyldimethylphosphine, propyldiphenylphosphine, tri(2,3-dichloropropyl)phosphine, tri(2,6-dimethylphenyl)phosphine, tri(2-chloroethyl)phosphine, tri (nonylphenyl)phosphine, tris(2,6-dimethylphenyl) phosphine, tris(2-methylphenyl)phosphine, tris(4-methylphenyl)phosphine, tris(methoxyphenyl)phosphine, tris[4-(1,1-dimethylethyl)phenyl]phosphine, or combinations thereof. In some embodiments, phosphines suitable for use in this disclosure include without limitation tributylphosphine, tricresyl phosphine, tricyclohexyl phosphine, tridecylphosphine, triethylphosphine, triheptylphosphine, triisopropylphosphine, trimethylphosphine, trioctadecyl phosphine, trioctylphosphine, tripentylphosphine, triphenylphosphine, tripropylphosphine, tri-t-butylphosphine, tritolylphosphine, trixylylphosphine, or combinations thereof.

In an embodiment, the organophosphorus compound precursor comprises phosphites, which can be represented by the general formula $(OR')_3P$; wherein each R' can be a hydrocarbyl group. Examples of phosphites suitable for use as phosphate precursors in this disclosure include without limitation (1-methylethyl)diphenylphosphite, 2-ethylphenyldiphenyl phosphite, 4-(diphenylmethyl)phenyl]diphenylphosphite, bis(2-methylphenyl)(2-methylpropyl)phosphite, butyldiethylphosphite, butyldimethylphosphite, butyldiphenylphosphite, butyldipropylphosphite, crecyldiphenylphosphite, cyclohexyldiphenylphosphite, decyldiethylphosphite, decyldimethylphosphite, decyldiphenylphosphite, dibutyl (2-methylphenyl)phosphite, dicyclohexylphenylphosphite, diethyl(3-methylphenyl)phosphite, ethyldibutylphosphite, ethyldimethylphosphite, ethyldioctylphosphite, ethyldiphenylphosphite, ethyldipropylphosphite, heptyldibutylphosphite, heptyldiethylphosphite, heptyldimethyl phosphite, heptyldipentylphosphite, heptyldiphenylphosphite, hexyldibutylphosphite, hexyldiethylphosphite, hexyldimethyl phosphite, hexyldipentylphosphite, hexyldiphenylphosphite, methylbis(4-methylphenyl)phosphite, methyldibutylphosphite, methyldidecylphosphite, methyldiethylphosphite, methyldiphenylphosphite, methyldipropylphosphite, octyldimethylphosphite, octyldiphenylphosphite, pentyldibutylphosphite, pentyldiethylphosphite, pentyldimethylphosphite, pentyldiphenylphosphite, phenyldibutylphosphite, phenyldiethylphosphite, phenyldimethylphosphite, phenyldipropylphosphite, propyldibutylphosphite, propyldimethylphosphite, propyldiphenylphosphite, tri(2-chloroethyl)phosphite, tri(nonylphenyl)phosphite, tris(2,3-dichloropropyl)phosphite, tris(2,6-dimethylphenyl)phosphite, tris (2-methylphenyl)phosphite, tris(4-methylphenyl)phosphite, tris(methoxyphenyl)phosphite, tris[4-(1,1-dimethylethyl)phenyl]phosphite, tri-t-butylphosphite, or combinations thereof. In some embodiments, phosphites suitable for use in this disclosure include without limitation tributylphosphite, tricresyl phosphite, tricyclohexyl phosphite, tridecylphosphite, triethylphosphite, triheptylphosphite, triisopropylphosphite, trimethylphosphite, trioctadecyl phosphite, trioctylphosphite, tripentylphosphite, triphenylphosphite, tripropylphosphite, tritolylphosphite, trixylylphosphite, or combinations thereof.

In an embodiment, the organophosphorus compound precursor comprises phosphinites, which can be represented by the general formula $(R)_2(OR')_1P$; wherein each R can be hydrogen, a hydrocarbyl group, or combinations thereof; and wherein each R' can be a hydrocarbyl group. Examples of phosphinites suitable for use as phosphate precursors in this disclosure include without limitation (1-methylethyl)diphenylphosphinite, 2-ethylphenyldiphenyl phosphinite, 4-(diphenylmethyl)phenyl]diphenylphosphinite, bis(2-methylphenyl)(2-methylpropyl)phosphinite, butyldiethylphosphinite, butyldimethylphosphinite, butyldiphenylphosphinite, butyldipropylphosphinite, crecyldiphenylphosphinite, cyclohexyldiphenylphosphinite, decyldiethylphosphinite, decyldimethylphosphinite, decyldiphenylphosphinite, dibutyl(2-methylphenyl)phosphinite, dicyclohexylphenylphosphinite, diethyl(3-methylphenyl) phosphinite, ethyldibutylphosphinite, ethyldimethylphosphinite, ethyldioctylphosphinite, ethyldiphenylphosphinite, ethyldipropylphosphinite, heptyldibutylphosphinite, heptyldiethylphosphinite, heptyldimethyl phosphinite, heptyldipentylphosphinite, heptyldiphenylphosphinite, hexyldibutylphosphinite, hexyldiethylphosphinite, hexyldimethyl phosphinite, hexyldipentylphosphinite, hexyldiphenylphosphinite, methylbis(4-methylphenyl)phosphinite, methyldibutylphosphinite, methyldidecylphosphinite, methyldiethylphosphinite, methyldiphenylphosphinite, methyldipropylphosphinite, octyldimethylphosphinite, octyldiphenylphosphinite, pentyldibutylphosphinite, pentyldiethylphosphinite, pentyldimethylphosphinite, pentyldiphenylphosphinite, phenyldibutylphosphinite, phenyldiethylphosphinite, phenyldimethylphosphinite, phenyldipropylphosphinite, propyldibutylphosphinite, propyldimethylphosphinite, propyldiphenylphosphinite, tri(2-chloroethyl)phosphinite, tri(nonylphenyl)phosphinite, tris (2,3-dichloropropyl)phosphinite, tris(2,6-dimethylphenyl) phosphinite, tris(2-methylphenyl)phosphinite, tris(4-methylphenyl)phosphinite, tris(methoxyphenyl) phosphinite, tris[4-(1,1-dimethylethyl)phenyl]phosphinite, tri-t-butylphosphinite, or combinations thereof. In some embodiments, phosphinites suitable for use in this disclosure include without limitation tributylphosphinite, tricresyl phosphinite, tricyclohexyl phosphinite, tridecylphosphinite, triethylphosphinite, triheptylphosphinite, triisopropylphosphinite, trimethylphosphinite, trioctadecyl phosphinite, trioctylphosphinite, tripentylphosphinite, triphenylphosphinite, tripropylphosphinite, tritolylphosphinite, trixylylphosphinite, or combinations thereof.

In an embodiment, the organophosphorus compound precursor comprises phosphonites, which can be represented by the general formula $(R)_1(OR')_2P$; wherein each R can be hydrogen, a hydrocarbyl group, or combinations thereof; and wherein each R' can be a hydrocarbyl group. Examples of phosphonites suitable for use as phosphate precursors in this disclosure include without limitation (1-methylethyl)diphenylphosphonite, 2-ethylphenyldiphenyl phosphonite, 4-(diphenylmethyl)phenyl]diphenylphosphonite, bis(2-methylphenyl)(2-methylpropyl)phosphonite, butyldiethylphosphonite, butyldimethylphosphonite, butyldiphenylphosphonite, butyldipropylphosphonite, crecyldiphenylphosphonite, cyclohexyldiphenylphosphonite, decyldiethylphosphonite, decyldimethylphosphonite, decyldiphenylphosphonite, dibutyl(2-methylphenyl)phosphonite, dicyclohexylphenylphosphonite, diethyl(3-methylphenyl)phosphonite, ethyldibutylphosphonite, ethyldimethylphosphonite, ethyldioctylphosphonite, ethyldiphenylphosphonite, ethyldipropylphosphonite, heptyldibutylphosphonite, heptyldiethylphosphonite, heptyldimethyl phosphonite, heptyldipentylphosphonite, heptyldiphenylphosphonite, hexyldibutylphosphonite, hexyldiethylphosphonite, hexyldimethyl phosphonite, hexyldipentylphosphonite, hexyldiphenylphosphonite, methylbis(4-methylphenyl)phosphonite, methyldibutylphosphonite, methyldidecylphosphonite, methyldiethylphosphonite, methyldiphenylphosphonite, methyldipropylphosphonite, octyldimethylphosphonite, octyldiphenylphosphonite, pentyldibutylphosphonite, pentyldiethylphosphonite, pentyldimethylphosphonite, pentyldiphenylphosphonite, phenyldibutylphosphonite, phenyldiethylphosphonite, phenyldimethylphosphonite, phenyldipropylphosphonite, propyldibutylphosphonite, propyldimethylphosphonite, propyldiphenylphosphonite, tri(2-chloroethyl)phosphonite, tri (nonylphenyl)phosphonite, tris(2,3-dichloropropyl)phosphonite, tris(2,6-dimethylphenyl)phosphonite, tris(2-methylphenyl)phosphonite, tris(4-methylphenyl) phosphonite, tris(methoxyphenyl)phosphonite, tris[4-(1,1-dimethylethyl)phenyl]phosphonite, tri-t-butylphosphonite, or combinations thereof. In some embodiments, phosphonites suitable for use in this disclosure include without limitation tributylphosphonite, tricresyl phosphonite, tricyclohexyl phosphonite, tridecylphosphonite, triethylphosphonite, triheptylphosphonite, triisopropylphosphonite, trimethylphosphonite, trioctadecyl phosphonite, trioctylphosphonite, tripentylphosphonite, triphenylphosphonite, tripropylphosphonite, tritolylphosphonite, trixylylphosphonite, or combinations thereof.

In an embodiment, the organophosphorus compound and/or organophosphorus compound precursor can be present in the mixture for the preparation of the SHC in an amount of from about 0.005 wt. % to about 5 wt. % based on the weight of phosphorus to the total weight of the SHC, alternatively from about 0.001 wt. % to about 1 wt. %, alternatively from about 0.01 wt. % to about 0.09 wt. %, or alternatively from about 0.02 wt. % to about 0.5 wt. %. The amount of organophosphorus compound and/or phosphorus incorporated into the SHC can be in the range described herein for the amount of organophosphorus compound and/or precursor used to prepare the SHC.

In an embodiment, the SHC further comprises a weak acid, alternatively a weak organic acid or alternatively a weak inorganic acid. In an embodiment, the weak organic acid comprises; organoboronic acids; carboxylic acids, such as acrylic acid, methacrylic acid, malonic acid, succinic acid, salicylic acid, adipic acid, maleic acid, malic acid, oleic acid, gallic acid, tartaric acid, citric acid, formic acid, acetic acid, glycolic acid, oxalic acid, tartaric acid (e.g., dextotartaric acid, mesotartaric acid, etc.), propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; phenols, such as pyrogallol (benzene-1,2,3-triol), pyrocatechol (benezenediol), or combinations thereof. In an embodiment, the weak inorganic acid comprises boric acid. In an embodiment, the weak organic acid comprises acetic acid.

In an embodiment, a weak acid suitable for use in the present disclosure is characterized by an acid dissociation constant ($pK_a$) in the range of from about 2.0 to about 12.0, alternatively from about 3.0 to about 10.0, or alternatively from about 4.0 to about 9.5.

In an embodiment, the weak acid can be present in the mixture for the preparation of the SHC in an amount of from about 0.00016 wt. % to about 0.16 wt. % based on the weight of hydrogen in dissociated proton form of the weak acid used to the total weight of the SHC, alternatively from about 0.00032 wt. % to about 0.032 wt. %, alternatively from about 0.00064 wt. % to about 0.029 wt. %, or alternatively from about 0.0016 wt. % to about 0.016 wt. %.

In an embodiment the weak acid can be present in the mixture for the preparation of the SHC in an amount that provides a molar ratio of weak acid:organophosphorus compound (or organophosphorus compound precursor) of about 0.1:1, alternatively about 0.5:1, alternatively about 1:1, alternatively about 2:1, or alternatively about 3:1.

In an embodiment, the SHC can further comprise one or more selectivity enhancers. Suitable selectivity enhancers include, but are not limited to, Group 1B metals, Group 1B metal compounds, silver compounds, gold compounds, fluorine, fluoride compounds, metals, alkali metal compounds, alkaline earth metals, alkaline earth metal compounds, iodine, iodide compounds, or combinations thereof. In an embodiment, the SHC comprises one or more selectivity enhancers which can be present in the mixture for preparation of the SHC in an amount of from about 0.001 wt. % to about 10 wt. % based on the total weight of the SHC, alternatively from about 0.01 wt. % to about 5 wt. %, alternatively from about 0.01 wt. % to about 2 wt. %. The amount of selectivity enhancer incorporated into the SHC can be in the range described herein for the amount of selectivity enhancer used to prepare the SHC.

In an embodiment, the selectivity enhancer comprises silver (Ag), silver compounds, or combinations thereof. Examples of suitable silver compounds include without limitation silver nitrate, silver acetate, silver bromide, silver chloride, silver iodide, silver fluoride, or combinations thereof. In an embodiment, the selectivity enhancer comprises silver nitrate. The SHC can be prepared using silver nitrate in an amount of from about 0.005 wt. % to about 5 wt. % silver based on the total weight of the SHC, alternatively from about 0.01 wt. % to about 1 wt. % silver, alternatively from about 0.02 wt. % to about 0.5 wt. %, alternatively from about 0.03 wt. % to about 0.3 wt. %. The amount of silver incorporated into the SHC can be in the range described herein for the amount of silver nitrate used to prepare the SHC.

In an embodiment, the selectivity enhancer comprises alkali metals, alkali metal compounds, or combinations thereof. Examples of suitable alkali metal compounds include without limitation elemental alkali metal, alkali metal halides (e.g., alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer comprises potassium fluoride (KF). In another embodiment, the SHC can be prepared using an alkali metal compound in an amount of from about 0.01 wt. % to about 5 wt. % based on the total weight of the SHC, alternatively from about 0.05 wt. % to about 2 wt. %, alternatively from about 0.05 wt. % to about 1 wt. %. The amount of alkali metal incorporated into the SHC can be in the range described herein for the amount of alkali metal compound used to prepare the SHC.

In an embodiment, a method of preparing a SHC can initiate with the contacting of an inorganic support with a palladium-containing compound to form a supported-palladium composition. The contacting can be carried out using any suitable technique. For example, the inorganic support can be contacted with a solution of the palladium-containing compound by soaking in a volume of solution of palladium-containing compound greater than the pore volume of the support or incipient wetness impregnation of the support. In such embodiments, the resulting supported-palladium composition can have greater than about 90 wt. %, alternatively from about 92 wt. % to about 98 wt. %, alternatively from about 94 wt. % to about 96 wt. % of the palladium concentrated near the periphery of the supported-palladium composition, as to form a palladium skin.

The palladium skin can be any thickness as long as such skin thickness can promote the hydrogenation processes disclosed herein. Generally, the thickness of the palladium skin can be in the range of from about 1 micron to about 3000 microns, alternatively from about 5 microns to about 2000 microns, alternatively from about 10 microns to about 1000 microns, alternatively from about 50 microns to about 500 microns. Examples of such methods are further described in more details in U.S. Pat. Nos. 4,404,124 and 4,484,015, each of which is incorporated by reference herein in its entirety.

Any suitable method can be used for determining the thickness of the palladium skin of the supported-palladium composition, selective hydrogenation catalyst and/or SHC composition. For example, one method involves breaking open a representative sample of the SHC and treating the catalyst pieces with a dilute alcoholic solution of N,N-dimethyl-para-nitrosoaniline. The treating solution can react with the palladium to give a red color that can be used to evaluate the distribution of the palladium on the catalyst. Yet another technique for measuring the concentration of the palladium in the skin of the SHC involves breaking open a representative sample of catalyst, followed by treating the catalyst pieces with a reducing agent such as hydrogen to change the color of the skin and thereby evaluate the distribution of the palladium. Alternatively, the palladium skin thickness can be determined by analyzing a cross-section of the catalyst using an electron microprobe analyzer.

The supported-palladium composition formed by contacting the inorganic support with a solution of a palladium-containing compound optionally can be dried at a temperature of from about 15° C. to about 150° C., alternatively from about 30° C. to about 100° C., or alternatively from about 60° C. to about 100° C.; and for a period of from about 0.1 hour to about 100 hours, alternatively from about 0.5 hour to about 20 hours, or alternatively from about 1 hour to about 10 hours. Alternatively, the supported-palladium composition can be calcined. This calcining step can be carried out at temperatures up to about 850° C., alternatively of from about 150° C. to about 700° C., alternatively from about 150° C. to about 600° C., or alternatively from about 150° C. to about 500° C.; and for a period of from about 0.2 hour to about 20 hours, alternatively from about 0.5 hour to about 20 hours, or alternatively from about 1 hour to about 10 hours. In an embodiment, the supported-palladium composition can be dried and subsequently calcined.

In an embodiment, a method of preparing a SHC further comprises contacting the supported-palladium composition with an organophosphorus compound of the type described herein (e.g., phosphine oxide, phosphate, an organophosphorus compound precursor such as an phosphate or an phosphine) and a weak acid.

In an embodiment, an organophosphorus compound of the type disclosed herein is contacted with one or more weak acids of the type disclosed herein. For example, the organophosphorus compound can be introduced to a solution of a weak acid (e.g., acetic acid, boric acid). The solution of weak acid and organophosphorus compound can then be contacted with the supported-palladium composition. The contacting can be carried out in any suitable manner that will yield a selective hydrogenation catalyst meeting the parameters described herein; such as for example by incipient wetness impregnation. Herein a SHC is formed by the contacting of a supported-palladium composition with an organophosphorus compound and weak acid is designated a Pd/OPC—H. Briefly, the organophosphorus compound can comprise phosphine oxide that is dissolved in a weak acid solution, such as for example, acetic acid, boric acid, citric acid, oxalic acid, etc., to form a phosphine oxide-containing weakly acidic solution. In an embodiment, the supported-palladium composition can be added to the phosphine oxide-containing weakly acidic solution to form an acidized palladium/phosphine oxide supported composition (herein this particular embodiment is referred to as a H—Pd/PO composition).

In an embodiment, silver can be added to the supported-palladium composition (without an organophosphorus compound and weak acid). For example, the supported-palladium composition can be placed in an aqueous silver nitrate solution of a quantity greater than that necessary to fill the pore volume of the composition. The resulting material is a supported palladium/silver composition (herein this particular embodiment is referred to as a Pd/Ag composition).

In an embodiment, the Pd/Ag composition is further contacted with an organophosphorus compound and weak acid. The contacting can be carried out as described above to form an H—Pd/Ag/OPC. In another embodiment, the Pd/Ag composition is further contacted with a phosphine oxide and weak acid (herein this particular embodiment is referred to as an H—Pd/Ag/PO composition).

In an embodiment, one or more alkali metals can be added to the Pd/Ag composition (prior to or following contacting with an organophosphorus compound and weak acid) using any suitable technique such as those described previously herein. In an embodiment, the selectivity enhancer comprises an alkali fluoride, and the resulting material is a palladium/silver/alkali metal fluoride supported composition.

In an embodiment, the supported-palladium composition is contacted with both an alkali metal halide and a silver compound (prior to or following contacting with an organophosphorus compound and weak acid). Contacting of the supported-palladium composition with both an alkali metal halide and a silver compound can be carried out simultaneously; alternatively, the contacting can be carried out sequentially in any user-desired order.

In an embodiment, one or more selectivity enhancers can be contacted with the supported-palladium composition prior to contacting the composition with an organophosphorus compound and weak acid. In such embodiments, the resulting composition comprising Pd/Ag, Pd/KF, or Pd/Ag/KF can be calcined under the conditions described previously herein, and subsequently contacted with an organophosphorus compound and weak acid. For example, phosphine oxide (PO) and a weak acid can be added to the Pd/Ag, Pd/KF, and/or Pd/Ag/KF compositions to provide H—Pd/Ag/PO, H—Pd/KF/PO, and/or H—Pd/Ag/KF/PO compositions, respectively. In an alternative embodiment, one or more selectivity enhancers can be contacted with the supported-palladium composition following contacting of the composition with an organophosphorus compound and weak acid. For example, Ag and/or KF can be added to the H—Pd/PO composition to provide H—Pd/Ag/PO, H—Pd/KF/PO, and/or H—Pd/Ag/KF/PO compositions. In yet another alternative embodiment, one or more selectivity enhancers can be contacted with the supported-palladium composition, an organophosphorus compound, and weak acid simultaneously.

In an embodiment, a method of preparing a SHC of the type disclosed comprises contacting an α-alumina support, palladium, an organophosphorus compound and a weak acid, each of the type previously disclosed herein. In an alternative embodiment, a method of preparing a SHC of the type disclosed herein comprises contacting an α-alumina support, palladium, an organophosphorus compound (e.g., phosphine oxide), a weak acid and one or more selectivity enhancers, (e.g., silver and/or potassium fluoride). The resultant materials (H—Pd/PO, H—Pd/Ag/PO, H—Pd/KF/PO, and/or the H—Pd/Ag/KF/PO compositions) can be dried to form a dried catalyst composition. In some embodiments, this drying step can be carried out at a temperature in the range of from about 0° C. to about 150° C., alternatively from about 30° C. to about 100° C., alternatively from about 50° C. to about 80° C.; and for a period of from about 0.1 hour to about 100 hours, alternatively from about 0.5 hour to about 20 hours, or alternatively from about 1 hour to about 10 hours at pressures ranging from ambient to 100 torr of vacuum. In an embodiment, the organophosphorus compound comprises an organophosphorus compound precursor that upon exposure to air and/or the temperature ranges used during drying of the aforementioned composition is converted to an organophosphorus compound of the type described herein. In some embodiments, this drying step can be carried out at ambient pressure, alternatively, this drying step can be carried out at a pressure from about 0.1 atm to 1 atm.

The dried catalyst composition can be reduced using hydrogen gas or a hydrogen gas containing feed, e.g., the feed stream of the selective hydrogenation process, thereby providing for optimum operation of the selective hydrogenation process to form a SHC. Such a gaseous hydrogen reduction can be carried out at a temperature in the range of from, for example, about 0° C. to about 150° C., alternatively 20° C. to about 100° C., or alternatively about 25° C. to about 80° C.

In an embodiment, a method of preparing a SHC comprises contacting an inorganic support with a palladium-containing compound (e.g., palladium chloride, palladium nitrate) to form a supported-palladium composition; and drying and calcining the supported-palladium composition to form a dried and calcined supported-palladium composition. The dried and calcined supported-palladium composition can then be contacted with a silver-containing compound (e.g., silver nitrite, silver fluoride) to form a Pd/Ag composition, which can then be dried and/or calcined to form a dried and/or calcined Pd/Ag composition. The dried and/or calcined Pd/Ag composition can be contacted with an alkali metal fluoride (e.g., potassium fluoride) to form a Pd/Ag/KF composition that is then dried and calcined. The dried and calcined Pd/Ag/KF composition can then be contacted with an organophosphorus compound (e.g., phosphine oxide or precursor) and weak acid to form a catalyst composition that is subsequently reduced to form a SHC.

In some embodiments, the SHC can be formed from a palladium/silver/alkali metal salt composition that has been contacted with an organophosphorus compound and weak acid. In some embodiments, the resultant material is a catalyst precursor that can be further treated to form a SHC. In some embodiments, further treatments comprise drying. In some embodiments, further treatments comprise reducing. In some embodiments, further treatments comprise drying and reducing.

In an embodiment, the SHC catalyzes a selective hydrogenation process. In such processes, the SHC can be contacted with an unsaturated hydrocarbon stream primarily containing unsaturated hydrocarbons, e.g., ethylene, but also containing a highly unsaturated hydrocarbon, e.g., acetylene. The contacting can be executed in the presence of hydrogen at conditions effective to selectively hydrogenate the highly unsaturated hydrocarbon to an unsaturated hydrocarbon. In an embodiment, SHCs of the type disclosed herein are used in the hydrogenation of highly unsaturated hydrocarbons such as for example and without limitation acetylene, methylacetylene, propadiene, butadiene or combinations thereof.

FIG. 1 illustrates an embodiment of a hydrogenation process that utilizes a SHC of the type disclosed herein. The hydrogenation process includes feeding an unsaturated hydrocarbon stream 10 and a hydrogen ($H_2$) stream 20 to a hydrogenation reactor 30 within which the SHC is disposed. The unsaturated hydrocarbon stream 10 primarily comprises one or more unsaturated hydrocarbons, but it can also contain one or more highly unsaturated hydrocarbons such as for example and without limitation acetylene, methylacetylene, propadiene, and butadiene. Alternatively, unsaturated hydrocarbon stream 10 and hydrogen stream 20 can be combined in a single stream that is fed to hydrogenation reactor 30.

In an embodiment, reactor 30 is a selective hydrogenation reactor that can belong to an acetylene removal unit of an unsaturated hydrocarbon production plant in a backend configuration. As used herein, "backend" refers to the location of the acetylene removal unit in an unsaturated hydrocarbon production unit that receives the lower boiling fraction from a deethanizer fractionation tower that receives the higher boiling fraction from a demethanizer fractionation tower that receives a feed from an unsaturated hydrocarbon production process.

In an embodiment, reactor 30 is a selective hydrogenation reactor that can belong to an acetylene removal unit of an unsaturated hydrocarbon production plant in a frontend deethanizer configuration. As used herein, "frontend deethanizer" refers to the location of the acetylene removal unit in an unsaturated hydrocarbon production unit that receives the lower boiling fraction from a deethanizer fractionation tower that receives a feed from an unsaturated hydrocarbon production process.

In an embodiment, reactor 30 is a selective hydrogenation reactor that can belong to an acetylene removal unit of an unsaturated hydrocarbon production plant in a frontend depropanizer configuration. As used herein, "frontend depropanizer" refers to the location of the acetylene removal unit in an unsaturated hydrocarbon production unit that receives the lower boiling fraction from a depropanizer fractionation tower that receives a feed from an unsaturated hydrocarbon production process.

In an embodiment, reactor 30 is a selective hydrogenation reactor that can belong to an acetylene removal unit of an unsaturated hydrocarbon production plant in a raw gas configuration. As used herein, "raw gas" refers to the location of the acetylene removal unit in an unsaturated hydrocarbon production unit that receives a feed from an unsaturated hydrocarbon production process without any intervening hydrocarbon fractionation.

It is understood that hydrogenation reactor 30, and likewise the selective hydrogenation catalysts disclosed herein, are not limited to use in backend acetylene removal units, frontend deethanizer units, frontend depropanizer, or raw gas units and can be used in any process wherein a highly unsaturated hydrocarbons contained within an unsaturated hydrocarbon stream is selectively hydrogenated to a unsaturated hydrocarbon.

In those embodiments wherein the acetylene removal unit is in a backend configuration, the highly unsaturated hydrocarbon being fed to the hydrogenation reactor 30 comprises acetylene. The mole ratio of the hydrogen to the acetylene being fed to hydrogenation reactor 30 can be in the range of from about 0.1 to about 10, alternatively from about 0.2 to about 5, alternatively from about 0.5 to about 3.

In those embodiments wherein the acetylene removal unit is in a front-end deethanizer, front-end depropanizer or raw gas configuration, the highly unsaturated hydrocarbon being fed to the hydrogenation reactor 30 comprises acetylene. In such an embodiment, the mole ratio of the hydrogen to the acetylene being fed to the hydrogenation reactor 30 can be in the range of from about 10 to about 3000, alternatively from about 10 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises methylacetylene. In such an embodiment, the mole ratio of the hydrogen to the methylacetylene being fed to the hydrogenation reactor 30 can be in the range of from about 3 to about 3000, alternatively from about 5 to about 2000, alternatively from about 10 to about 1500.

In those embodiments wherein the acetylene removal unit is in a front-end depropanizer or raw gas configuration, the highly unsaturated hydrocarbon being fed to the hydrogenation reactor 30 comprises propadiene. In such an embodiment, the mole ratio of the hydrogen to the propadiene being fed to the hydrogenation reactor 30 can be in the range of from about 3 to about 3000, alternatively from about 5 to about 2000, alternatively from about 10 to about 1500.

In another embodiment, reactor 30 can represent a plurality of reactors. The plurality of reactors can optionally be separated by a means to remove heat produced by the reaction. The plurality of reactors can optionally be separated by a means to control inlet and effluent flows from reactors or heat removal means allowing for individual or alternatively groups of reactors within the plurality of reactors to be regenerated. The selective hydrogenation catalyst can be arranged in any suitable configuration within hydrogenation reactor 30, such as a fixed catalyst bed.

Carbon monoxide can also be fed to reactor 30 via a separate stream (not shown), or it can be combined with hydrogen stream 20. In an embodiment, the amount of carbon monoxide being fed to reactor 30 during the hydrogenation process is less than about 0.15 mol % based on the total moles of fluid being fed to reactor 30.

Hydrogenation reactor 30 can be operated at conditions effective for selective hydrogenation of the highly unsaturated hydrocarbons to one or more unsaturated hydrocarbons upon contacting the selective hydrogenation catalyst in the presence of the hydrogen. The conditions are desirably effective to maximize hydrogenation of highly unsaturated hydrocarbons to unsaturated hydrocarbons and to minimize hydrogenation of highly unsaturated hydrocarbons to saturated hydrocarbons. In some embodiments, acetylene can be selectively hydrogenated to ethylene. Alternatively, methylacetylene can be selectively hydrogenated to propylene; alternatively, propadiene can be selectively hydrogenated to propylene. Alternatively, butadiene can be selectively hydrogenated to butenes. In some embodiments, the temperature within the hydrogenation zone can be in the range of from about 5° C. to about 300° C., alternatively from about 10° C. to about 250° C., alternatively from about 15° C. to about 200° C. In some embodiments, the pressure within the hydrogenation zone can be in the range of from about 15 (204 kPa) to about 2,000 (13,890 kPa) pounds per square inch gauge (psig), alternatively from about 50 psig (446 kPa) to about 1,500 psig (10,443 kPa), alternatively from about 100 psig (790 kPa) to about 1,000 psig (6,996 kPa).

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment, effluent stream 40 primarily comprises ethylene comprises less than about 5 ppmw, alternatively less than about 1 ppmw of highly unsaturated hydrocarbons.

In an embodiment, a SHC of the type describe herein can have a comparable catalytic activity when compared to an otherwise similar selective hydrogenation catalyst prepared in the absence of an organophosphorus compound and weak acid. The comparable catalytic activity can translate to a comparable clean up temperature. Herein, the clean-up temperature is designated T1 and refers to the temperature at which the acetylene concentration drops below 20 ppmw in a feed stream comprising unsaturated hydrocarbon and highly unsaturated hydrocarbons such as acetylenes and diolefins. In an embodiment, a SHC of the type disclosed herein can have a T1 of from about 80° F. to about 160° F., alternatively from about 85° F. to about 145° F., alternatively from about 90° F. to about 130° F.

In an embodiment, a SHC of the type disclosed herein displays enhanced sulfur resistance. Herein "enhanced" sulfur resistance refers to the improvement in the recovered catalyst activity as compared to the activity before exposure to sulfur-containing materials from the feed. Herein "enhanced" sulfur resistance may also refer to the reduced amount of time required for the catalyst activity to recover.

In an embodiment, a SHC can exhibit an increased selectivity when compared to an otherwise similar SHC prepared in the absence of an organophosphorus compound and weak acid. Herein selectivity refers to a comparison between the rate at which the SHC converts a highly unsaturated hydrocarbon to an unsaturated hydrocarbon, herein termed Conversion 1, and the rate at which the SHC converts an unsaturated hydrocarbon to a saturated hydrocarbon, herein termed Conversion 2. A SHC can display an increased rate of Conversion 1 and a decreased rate of Conversion 2 when compared to an otherwise similar catalyst prepared in the absence of an organophosphorus compound and weak acid of the type described herein. Conversion 2 is highly exothermic and can lead to runaway reactions or the uncontrollable conversion of unsaturated hydrocarbons to saturated hydrocarbons due to the presence of excess unsaturated hydrocarbons. The higher selectivity of the SHC can result in a reduction in the incidence of runaway reactions and increase the operating window of the hydrogenation process.

An operating window ($\Delta T$) is defined as the difference between a runaway temperature (T2) at which 3 wt % of ethylene is hydrogenated from a feedstock comprising highly unsaturated and unsaturated hydrocarbons, and the clean-up temperature (T1). $\Delta T$ is a convenient measure of the operational stability of a selective hydrogenation catalyst for the hydrogenation of highly unsaturated hydrocarbons (e.g., acetylene) to unsaturated hydrocarbons (e.g., ethylene). The more stable a hydrogenation catalyst, the higher the temperature beyond T1 required to hydrogenate a given unsaturated hydrocarbons (e.g., ethylene). The T2 is coincident with the temperature at which a high probability exists for a runway ethylene hydrogenation reaction to occur in an adiabatic reactor. Therefore, a larger $\Delta T$ translates to a more stable catalyst and a wider operation window for the complete acetylene hydrogenation.

In an embodiment, a SHC of the type disclosed herein can have an operating window of from about 25° F. to about 120° F., alternatively from about 30° F. to about 125° F., or alternatively from about 35° F. to about 1300° F. The operating window of a SHC of the type described herein can be increased by greater than about 10%, alternatively greater than about 15%, alternatively greater than about 20%, or alternatively greater than about 50% when compared to an otherwise similar catalyst prepared in the absence of an organophosphorus compound and weak acid. Selectivity typically refers to the percent ethylene conversion of acetylene at T1.

In an embodiment, a SHC of the type described herein when used as a hydrogenation catalyst can produce a reduced amount of heavies. As used herein, heavies refer to molecules having four or more carbon atoms per molecule ($C_{4+}$). Selective hydrogenation catalysts can produce heavies by oligomerizing the highly unsaturated hydrocarbons (e.g., acetylenes and diolefins) that are present in the feed stream. The presence of heavies is one of a number of contributors to the fouling of the selective hydrogenation catalysts that result in catalyst deactivation. The deactivation of the selective hydrogenation catalyst results in the catalyst having a lower activity and selectivity to unsaturated hydrocarbons. In an embodiment, a SHC of the type described herein exhibits a reduction in the weight percent $C_{4+}$ produced at T1 of from about 1 wt. % to about 25 wt. % alternatively from about 1.5 wt. % to about 20 wt. %, or alternatively from about 2 wt. % to about 15 wt. % when compared to the weight percent $C_{4+}$ produced at T1 of a catalyst composition not containing the organophosphorus compound.

In an embodiment, a SHC is prepared utilizing a weak acid and an organophosphorus compound having a low boiling point. Herein, the organophosphorus compound having a low boiling point is referred to as an "LBP organophosphorus compound." In such embodiments, the SHC can display activity comparable to or greater than an otherwise similar SHC prepared in the absence of an organophosphorus compound and weak acid. In an embodiment, a SHC comprising a supported-palladium catalyst composition with an LBP organophosphorus compound and weak acid, both of the type described herein can result in the catalyst displaying a selectivity and activity comparable to that of a hydrogenation catalyst comprising one or more selectivity enhancers (e.g., Pd/Ag, Pd/KF, or Pd/Ag/KF). In another embodiment, treatment of a hydrogenation catalyst comprising a single selectivity enhancer (e.g., Pd/Ag or Pd/KF) with an LBP organophosphorus compound and weak acid both of the type described herein can result in the catalyst displaying a selectivity and activity comparable to that of a hydrogenation catalyst comprising at least two selectivity enhancers (e.g., Pd/Ag/KF).

A method for the selective hydrogenation of a hydrocarbon feed comprising highly unsaturated and unsaturated hydrocarbons can comprise the preparation of a SHC catalyst comprising a LBP organophosphorus compound and weak acid, both of the type disclosed herein, and contacting of the SHC with the hydrocarbon feed in a reactor having an initial temperature (T0). The LBP organophosphorus compound and weak acid can remain associated with the SHC upon start of the reaction at T0, however, over time and as the temperature increases above the boiling point of the LBP organophosphorus compound, the LBP organophosphorus compound can be evaporated (i.e., boiled off) from the SHC. Depending on the boiling point, the weak acid can also be evaporated (i.e., boiled off) from the SHC. The SHC prepared utilizing the LBP organophosphorus compound and weak acid can display an increased activity over time and an enhanced initial selectivity when the LBP organophosphorus compound and weak acid is associated or has been associated with the SHC. This can be advantageous for reactions employing a fresh catalyst as a SHC prepared utilizing the LBP organophosphorus compound and weak acid can allow for a more stable operation and a reduction in the potential for a runaway reaction due to the increase in catalyst selectivity and predictable catalytic activity as the composition stabilizes. In other words, the presence of the SHC prepared utilizing the LBP organophosphorus compound and weak acid can aid in the control of the reaction during start up following a catalyst change out. Following the loss of the LBP organophosphorus compound, the resulting composition can display an activity and selectivity comparable to that of an otherwise similar catalyst prepared in the absence of an organophosphorus compound and weak acid.

In an alternative embodiment, a method for the selective hydrogenation of a hydrocarbon feed comprising highly unsaturated and unsaturated hydrocarbons comprises the preparation of a SHC comprising a weak acid and a high boiling point organophosphorus compound, both of the type described previously herein, and contacting of the SHC with the hydrocarbon feed. The high boiling point organophosphorus compound can remain associated with the SHC throughout the lifetime of the catalyst providing the reaction temperature remains below the boiling point of the high boiling point organophosphorus compound. The SHC prepared utilizing the high boiling point organophosphorus compound and weak acid can display improvements in characteristics such as catalytic activity and selectivity when compared to an otherwise similar catalyst composition prepared in the absence of an organophosphorus compound and weak acid.

In an alternative embodiment, a method for the selective hydrogenation of a hydrocarbon feed comprising highly unsaturated and unsaturated hydrocarbons comprises the preparation of a SHC comprising a weak acid, a high boiling point organophosphorus compound, and a low boiling point organophosphorus each of the type described previously herein, and contacting of the SHC with the hydrocarbon feed. The SHC prepared utilizing both the low boiling point organophosphorus compound, and the high boiling point organophosphorus compound along with the weak acid can display the improvements in characteristics such as catalytic activity and selectivity when compared to an otherwise similar catalyst composition prepared in the absence of an organophosphorus compound and weak acid. Further, these SHCs can be advantageous for reactions employing a fresh catalyst as a SHC can allow for a more stable operation and a reduction in the potential for runaway reactions due to the increase in catalyst selectivity and predictable catalytic activity as the composition stabilizes.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

Example 1

A control catalyst sample, Catalyst A, was prepared on a commercial Pd/Ag catalyst/$\alpha$-$Al_2O_3$ pellets supplied by Süd Chemie of, Huefeld Germany in the form of 4 mm×4 mm tablets as described in U.S. Pat. No. 4,484,015 which is incorporated by reference herein in its entirety. The $\alpha$-$Al_2O_3$ pellets had a surface area of about 5 to about 7 $m^2/g$ (determined by the BET method employing $N_2$ adsorption). Next 100 g of the commercial Pd/Ag catalyst was then impregnated with a solution of 0.45 g KF dissolved in 27.8 g of water ($H_2O$). The catalyst was then dried at 90° C. for 1 hour, at 200° C. for 1 hour, at 400° C. for 1 hour, and at 540° C. for 3 hours resulting in a catalyst comprising 230 ppm by weight (ppmw) palladium and 920 ppmw silver 3000 ppmw potassium.

Catalyst B was prepared by adding a solution of 0.21 g tributyl phosphine oxide (TBPO) in 25.5 g of water to 100 g of Catalyst A. Catalyst B was then vacuum filtered then dried overnight by drawing air through the catalyst with the vacuum. Catalyst B contained 0.03 wt. % of phosphorus. Catalyst C was prepared by adding a solution of 0.21 g tributyl phosphine oxide (TBPO) and 0.058 g glacial acetic acid in 25.5 g of water to 100 g of Catalyst A. Catalyst C was then vacuum filtered then dried overnight by drawing air through the catalyst with the vacuum. Catalyst C contained 0.03 wt. % of phosphorus. Catalyst D was prepared by adding a solution of 0.21 g tributyl phosphine oxide (TBPO) and 0.12 g boric acid in 25.5 g of water to 100 g of Catalyst A. Catalyst D was then vacuum filtered then dried overnight by drawing air through the catalyst with the vacuum. Catalyst D contained 0.03 wt. % of phosphorus. The data is summarized in Table 1.

TABLE 1

| Catalyst | Acid | mol acid/g catalyst | $k_a$ | H(dissociated)/P mol/mol |
|---|---|---|---|---|
| A | None | None | None | None |
| B | None | None | None | None |
| C | Acetic acid | $9.68 \times 10^{-6}$ | $1.76 \times 10^{-5}$ | 1:1 |
| D | Boric acid | $1.94 \times 10^{-5}$ | $5.8 \times 10^{-10}$ | 2:1 |

Example 2

The following examples describe how the sulfur testing was performed. A catalyst was first tested for initial fresh catalyst activity. The catalyst was then exposed to a sulfur rich hydrogen stream in-situ, and subsequently the catalyst was purged at an elevated temperature for a prolonged time with periodic testing to determine if activity had returned to its pre-sulfur exposure levels.

The catalyst was evaluated by placing 20 ml of catalyst sample inside a stainless steel reactor with 0.65 inches inside diameter. A thermowell of 3/16 inches diameter was inserted through the catalyst bed. The reactor temperature was regulated by circulating a heating medium, which contained a mixture of ethylene glycol and water, through the exterior shell of the reactor. The catalyst was first reduced at about 100° F. to 200° F. for about 1 to 2 hours under hydrogen gas flowing at 200 ml/min at 200 pounds per square inch gauge (psig). Then a synthetic feed was continuously introduced to the reactor at a flow rate of 900 mL per minute at 200 psig while holding the temperature constant before sampling the exit stream by gas chromatography. The catalyst temperature was determined by inserting a thermocouple into the thermowell and varying its position until the highest temperature was observed. The temperature of the heating medium was then raised a few degrees, and the testing cycle was repeated until the clean-up temperature is determined. The clean-up temperature, T1, is defined as the temperature at which the acetylene concentration in the exit stream falls below 20 ppmv.

The synthetic feed used in these examples is typical of a feed from the top of a deethanizer fractionation tower in an ethylene plant. With the exception that ethane was replaced with methane in the synthetic feed so that any ethane found in the reactor effluent was the result of the hydrogenation of ethylene. The synthetic feed contained approximately 25.8 mole percent methane, 47.4 mole percent ethylene, 0.16 mole percent acetylene, 26.6 mole percent hydrogen, 0.034 mole percent carbon monoxide.

After the activity test the reactor was purged with hydrogen. Next, the catalyst was poisoned with sulfur containing compound by passing about 100 ppmv of hydrogen sulfide with the balance being hydrogen at a flow rate of about 900 mL/min at ambient pressure over the catalyst at about 212° F. (100° C.) for about 4 or about 6 hours. After the sulfur poisoning treatment, the reactor system was purged with nitrogen to remove gaseous hydrogen sulfide remaining in the reactor system.

Figure 2:
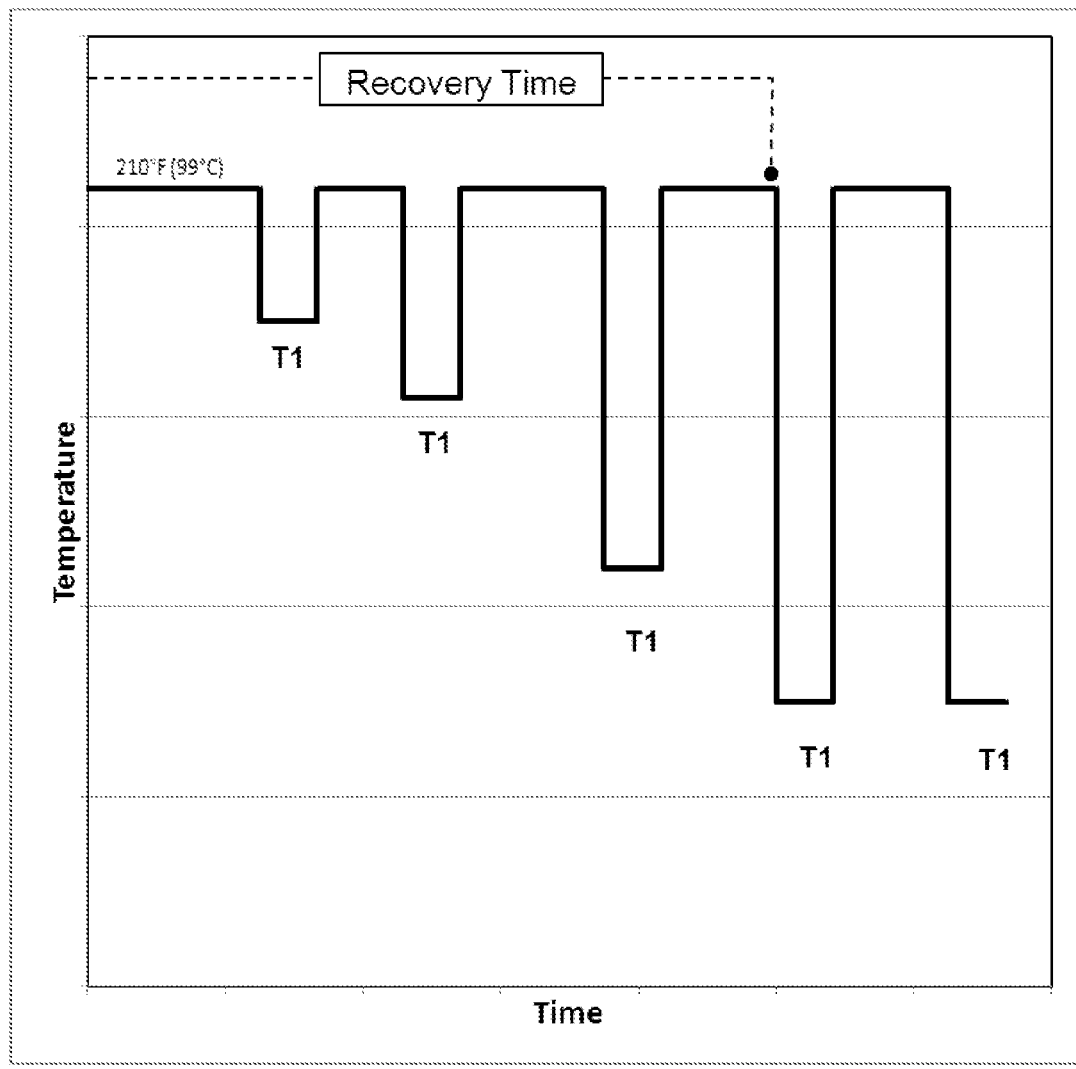
FIG. 2 depicts a plot of the recovery time for the samples from Example 2.

The poisoned catalyst requires purging to remove the sulfur. The time it takes to remove the sulfur by purging is inversely proportional to the sulfur resistance of the catalyst. In this relationship longer purging times indicate a less sulfur resistant catalyst and vice versa. The synthetic feed was contacted with the catalyst at a flow rate of about 900 mL/min at about 200 psig (1480 kPa) and at 210° F. (99° C.) for six hours. Following the six hours of purging, the recovered catalyst activity was determined by lowering the reactor temperature and measuring the cleanup temperature (T1). This measurement took about 2-3 hours. After the first measurement of T1 the reactor temperature was again raised to 210° F. (99° C.) for 5 hours. Again following the 5 hours of purging the temperature was again lowered and the T1 temperature was measured a second time. After this second measurement of T1 the reactor temperature was raised to 210° F. (99° C.) for 5 hours. Again following the 5 hours of purging, the temperature was again lowered and the T1 temperature was measured a third time to determine the recovered activity. After the third measurement of T1 the reactor temperature was again raised to 210° F. (99° C.) for 4 hours. Again, following the 4 hours of purging, the temperature was again lowered and the T1 temperature was measured for the fourth time to determine the recovered activity. From this point on the reactor temperature was repeatedly raised to 210° F. (99° C.) for 4 hours and then the temperature was lowered and the T1 temperature measured until the same T1 temperature was measured. The recovery time reported in Table 1 is the time between the start of the selective hydrogenation reaction at 212° F. (100° C.) and the time the temperature was lowered to measure the first T1 that was repeated as shown in FIG. 2.

Sulfur recovery tests were carried out for all catalysts prepared along with the control catalyst. The results are shown in Table 2.

TABLE 2

| Catalyst | Acid | Fresh catalyst T1 ° F. (° C.) | Time (hours) of sulfur treatment in 100 ppmw H$_2$S/H$_2$ (balance) feed at 212° F. | Recovered catalyst T1 ° F. (° C.) | Time (hours) of recovery reaction at 210° F. | Recovered activity as a percent of fresh catalyst activity |
|---|---|---|---|---|---|---|
| A | None | 112 (44.4) | 4 | 121 (49.4) | 16 | 68% |
| B | None | 110 (43.3) | 4 | 138 (58.9) | 20 | 31% |
| C | Weak organic acid | 109 (42.8) | 6 | 124 (51.1) | 16 | 65% |
| D | Weak inorganic acid | 111 (43.9) | 4 | 128 (53.3) | 20 | 48% |

The results first showed that the SHC catalyst with an added TBPO compound (Catalyst B) will cause the catalyst being more sensitive to sulfur poisoning as compared to catalyst without TBPO compound (Catalyst A). However, the results also demonstrate that the SHC catalyst with an added weak organic acid (Catalyst C) or with an added weak inorganic acid (Catalyst D) to the TBPO added catalyst showed an improved sulfur recovery as compared to the catalyst without added weak acid (Catalyst B).

The following are enumerated embodiments are provided as non-limiting examples.

A first embodiment which is a method of making a selective hydrogenation catalyst comprising contacting a support with a palladium-containing compound to form a supported-palladium composition; contacting the supported-palladium composition with an organophosphorus compound and a weak acid to form a selective hydrogenation catalyst composition; and reducing the selective hydrogenation catalyst composition to form the catalyst.

A second embodiment which the method of the first embodiment wherein the organophosphorus compound is represented by the general formula $(R)_x(OR')_yP=O$, wherein x and y are integers ranging from 0 to 3 and x plus y equals 3, wherein each R is hydrogen, a hydrocarbyl group, or combinations thereof; and wherein each R' is a hydrocarbyl group.

A third embodiment which is the method of any of the first through second embodiments wherein the organophosphorus compound comprises a phosphine oxide, a phosphinate, a phosphonate, a phosphate, or combinations thereof.

A fourth embodiment which is the method of any of the first through third embodiments wherein the organophosphorus compound is a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group.

A fifth embodiment which is the method of the fourth embodiment wherein the organophosphorus compound precursor comprises a phosphite, a phosphonite, a phosphinite, a phosphine, an organic phosphine, or combinations thereof.

A sixth embodiment which is the method of any of the first through fifth embodiments wherein the organophosphorus compound has a boiling point of greater than about 100° C.

A seventh embodiment which is the method of any of the first through sixth embodiments wherein the organophosphorus compound has a boiling point of equal to or less than about 100° C.

An eighth embodiment which is the method of any of the first through seventh embodiments wherein the weak acid comprises boric acid, carboxylic acids, or combinations thereof.

A ninth embodiment which is the method of any of the first through eighth embodiments wherein the weak acid comprises acrylic acid, methacrylic acid, malonic acid, succinic acid, salicylic acid, adipic acid, maleic acid, malic acid, oleic acid, gallic acid, tartaric acid, citric acid, formic acid, acetic acid, glycolic acid, oxalic acid, tartaric acid, dextotartaric acid, mesotartaric acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic, a phenol, pyrogallol (benzene-1,2,3-triol), pyrocatechol (benezenediol), organoboronic acids, or combinations thereof.

A tenth embodiment which is the method of any of the first through ninth embodiments wherein the weak acid is characterized by an acid dissociation constant pKa value in the range of from about 2 to about 12 in water.

An eleventh embodiment which is the method of any of the first through tenth embodiments wherein the weak acid is present in an amount of from about 0.00016 wt. % to about 0.16 wt. % based on the weight of hydrogen in dissociated proton form of the weak acid used to the total weight of the selective hydrogenation catalyst.

A twelfth embodiment which is the method of any of the first through eleventh embodiments wherein the palladium-containing compound is present in an amount of from about 0.005 wt. % to about 5 wt. % Pd based on the total weight of the catalyst; the organophosphorus compound is present in an amount of from about 0.005 wt. % to about 5 wt. % based on the total weight of the selective hydrogenation catalyst; and the weak acid is present in an amount to provide a weak acid to organophosphorus compound molar ratio is from 1:1 to 3:1.

A thirteenth embodiment which is the method of any of the first through twelfth embodiments wherein the selective hydrogenation catalyst comprises one or more selectivity enhancers.

A fourteenth embodiment which is the method of the thirteenth embodiment wherein the one or more selectivity enhancers is selected from the group consisting of Group 1B metals, Group 1B metal compounds, silver compounds, fluorine, fluoride compounds, sulfur, sulfur compounds, alkali metal, alkali metal compounds, alkaline earth metals, alkaline earth metal compounds, iodine, iodide compounds, and combinations thereof.

A fifteenth embodiment which is the method of the fourteenth embodiment wherein the silver compounds further comprise elemental silver, silver nitrate, silver acetate, silver bromide, silver chloride, silver iodide, silver fluoride, or combinations thereof.

A sixteenth embodiment which is the method of any the thirteenth through fifteenth embodiments wherein the selectivity enhancer is present in an amount of from about 0.005 wt. % to about 5 wt. % based on the support.

A seventeenth embodiment which is the method of the fourteenth embodiment wherein the alkali metal compounds comprise elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or combinations thereof.

An eighteenth embodiment which the method of the seventeenth embodiment wherein the alkali metal compound is present in an amount of from about 0.01 wt. % to about 5 wt. % based on the total weight of the selective hydrogenation catalyst.

A nineteenth embodiment which is the method of any of the first through eighteenth embodiments further comprising drying the selective hydrogenation catalyst precursor at a temperature of from about 0° C. to about 150° C. for a time period of from about 0.1 hour to about 100 hours.

A twentieth embodiment which is the method of any of the first through nineteenth embodiments wherein the support comprises one or more aluminas, silicas, titanias, zirconias, aluminosilicates, spinels, or combinations thereof.

A twenty-first embodiment which is a selective hydrogenation catalyst prepared according to the method of any of the first through twentieth embodiments.

A twenty-second embodiment which is a method of making a selective hydrogenation catalyst comprising contacting an alumina support with a palladium-containing compound to form a supported-palladium composition; contacting the supported-palladium composition with silver nitrate and potassium fluoride to form a mixture; contacting the mixture with an organophosphorus compound and a weak acid to form a selective hydrogenation catalyst precursor; and reducing the selective hydrogenation catalyst precursor to form the selective hydrogenation catalyst.

A twenty-third embodiment which is a composition comprising (i) a supported hydrogenation catalyst comprising palladium, a weak acid and a support, wherein the supported hydrogenation catalyst is capable of selectively hydrogenating highly unsaturated hydrocarbons to unsaturated hydrocarbons, the support has a surface area of from about 2 m$^2$/g to about 100 m$^2$/g, and greater than about 90 wt. % of the palladium is concentrated near a periphery of the support; and (ii) an organophosphorus compound.

A twenty-fourth embodiment which is the composition of the twenty-third embodiment wherein the organophosphorus compound comprises a phosphine oxide, phosphinate, phosphonate, phosphate, or combinations thereof.

A twenty-fifth embodiment which is the composition of any of the twenty-third through twenty-fourth embodiments wherein the organophosphorus compound is a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group.

A twenty-sixth embodiment which is the composition of the twenty-fifth embodiment wherein the organophosphorus compound precursor comprises a phosphite, a phosphonite, a phosphinite, a phosphine, an organic phosphine, or combinations thereof.

A twenty-seventh embodiment which is the composition of any of the twenty-third through twenty-sixth embodiments further comprising Group 1B metals, Group 1B metal compounds, silver compounds, fluorine, fluoride compounds, sulfur, sulfur compounds, alkali metal, alkali metal compounds, alkaline earth metals, alkaline earth metal compounds, iodine, iodide compounds, or combinations thereof.

A twenty-eighth embodiment which is the composition of any of the twenty-third through twenty-seventh embodiments wherein the phosphine oxide comprises tributylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, or combinations thereof.

A twenty-ninth embodiment which is the composition of any of the twenty-third through twenty-eighth embodiments wherein the weak acid comprises boric acid, carboxylic acids, or combinations thereof.

A thirtieth embodiment which is the composition of any of the twenty-third through twenty-ninth embodiments wherein the weak acid comprises acrylic acid, methacrylic acid, malonic acid, succinic acid, salicylic acid, adipic acid, maleic acid, malic acid, oleic acid, gallic acid, tartaric acid, citric acid, formic acid, acetic acid, glycolic acid, oxalic acid, tartaric acid, dextotartaric acid, mesotartaric acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic; a phenol, pyrogallol (benzene-1,2,3-triol), pyrocatechol (benzenediol), organoboronic acids, or combinations thereof.

A thirty-first embodiment which is the method of any of the twenty-third through thirtieth embodiments wherein the weak acid is characterized by an acid dissociation constant pKa value in the range of from about 2 to about 12 in water.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The disclosures of all patents, patent applications, and publications cited herein are hereby incorporated by reference, to the extent that they provide exemplary, procedural or other details supplementary to those set forth herein.

What is claimed is:

1. A method of making a selective hydrogenation catalyst comprising:
    contacting a support with a palladium-containing compound to form a supported-palladium composition;
    contacting the supported-palladium composition with an organophosphorus compound and a weak acid to form a selective hydrogenation catalyst composition, wherein the weak acid is present in an amount to provide a weak acid to organphosphorus compound molar ratio from 1:1 to 3:1; and
    reducing the selective hydrogenation catalyst composition to form the selective hydrogenation catalyst.

2. The method of claim 1 wherein the organophosphorus compound is represented by the general formula $(R)_x(OR')_yP=O$, wherein x and y are integers ranging from 0 to 3 and x plus y equals 3, wherein each R is hydrogen, a hydrocarbyl group, or combinations thereof; and wherein each R' is a hydrocarbyl group.

3. The method of claim 1 wherein the organophosphorus compound comprises a phosphine oxide, a phosphinate, a phosphonate, a phosphate, or combinations thereof.

4. The method of claim 1 wherein the organophosphorus compound is a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group.

5. The method of claim 4 wherein the organophosphorus compound precursor comprises a phosphite, a phosphonite, a phosphinite, a phosphine, an organic phosphine, or combinations thereof.

6. The method of claim 1 wherein the organophosphorus compound has a boiling point of greater than about 100° C.

7. The method of claim 1 wherein the organophosphorus compound has a boiling point of equal to or less than about 100° C.

8. The method of claim 1 wherein the weak acid comprises boric acid, carboxylic acids, or combinations thereof.

9. The method of claim 1 wherein the weak acid comprises acrylic acid, methacrylic acid, malonic acid, succinic acid, salicylic acid, adipic acid, maleic acid, malic acid, oleic acid, gallic acid, tartaric acid, citric acid, formic acid, acetic acid, glycolic acid, oxalic acid, tartaric acid, dextotartaric acid, mesotartaric acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxyhenzoic acid, aminobenzoic; a phenol, pyrogallol (benzene-1,2,3-triol), pyrocatechol (benezenediol), organoboronic acids, or combinations thereof.

10. The method of claim 1 wherein the weak acid is characterized by an acid dissociation constant pKa value in the range of from about 2 to about 12 in water.

11. The method of claim 1 wherein the weak acid is present in an amount of from about 0.00016 wt. % to about 0.16 wt. % based on the weight of hydrogen in dissociated proton form of the weak acid used to the total weight of the selective hydrogenation catalyst.

12. The method of claim 1 wherein:
the palladium-containing compound is present in an amount of from about 0.005 wt. % to about 5 wt. % Pd based on the total weight of the selective hydrogenation catalyst; and
the organophosphorus compound is present in an amount of from about 0.005 wt. % to about 5 wt. % based on the total weight of the selective hydrogenation catalyst.

13. The method of claim 1 wherein the selective hydrogenation catalyst comprises one or more selectivity enhancers.

14. The method of claim 13 wherein the one or more selectivity enhancers is selected from the group consisting of Group 1B metals, Group 1B metal compounds, silver compounds, fluorine, fluoride compounds, sulfur, sulfur compounds, alkali metal, alkali metal compounds, alkaline earth metals, alkaline earth metal compounds, iodine, iodide compounds, and combinations thereof.

15. The method of claim 14 wherein the silver compounds comprise elemental silver, silver nitrate, silver acetate, silver bromide, silver chloride, silver iodide, silver fluoride, or combinations thereof.

16. The method of claim 13 wherein the selectivity enhancer is present in an amount of from about 0.005 wt. % to about 5 wt. % based on weight of the support.

17. The method of claim 14 wherein the alkali metal compounds comprise elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or combinations thereof.

18. The method of claim 17 wherein the alkali metal compound is present in an amount of from about 0.01 wt. % to about 5 wt. % based on the total weight of the selective hydrogenation catalyst.

19. The method of claim 1 further comprising drying the selective hydrogenation catalyst precursor at a temperature of from about 0° C. to about 150° C. for a time period of from about 0.1 hour to about 100 hours.

20. The method of claim 1 wherein the support comprises one or more aluminas, silicas, titanias, zirconias, aluminosilicates, spinels, or combinations thereof.

21. A selective hydrogenation catalyst prepared according to the method of claim 1.

22. A composition comprising:
(i) a supported hydrogenation catalyst comprising palladium and a support, wherein the supported hydrogenation catalyst is capable of selectively hydrogenating highly unsaturated hydrocarbons to unsaturated hydrocarbons, the support has a surface area of from about 2 $m^2/g$ to about 100 $m^2/g$, and greater than about 90 wt. % of the palladium is concentrated near a periphery of the support; and
(ii) an organophosphorus compound and a weak acid, wherein the weak acid is present in an amount to provide a weak acid to organophosphorus compound molar ratio from 1:1 to 3:1.

23. The composition of claim 22 wherein the organophosphorus compound comprises a phosphine oxide, phosphinate, phosphonate, phosphate, or combinations thereof.

24. The composition of claim 22 wherein the organophosphorus compound is a product of an organophosphorus compound precursor represented by the general formula of $(R)_x(OR')_yP$, wherein x and y are integers ranging from 0 to 3 and x plus y equals 3, wherein each R is hydrogen, a hydrocarbyl group, or combinations thereof; and wherein each R' is a hydrocarbyl group.

25. The composition of claim 24 wherein the organophosphorus compound precursor comprises a phosphite, a phosphonite, a phosphinite, a phosphine, an organic phosphine, or combinations thereof.

26. The composition of claim 22 further comprising Group 1B metals, Group 1B metal compounds, silver compounds, fluorine, fluoride compounds, sulfur, sulfur compounds, alkali metal, alkali metal compounds, alkaline earth metals, alkaline earth metal compounds, iodine, iodide compounds, or combinations thereof.

27. The composition of claim 23 wherein the phosphine oxide comprises tributylphosphine oxide, triethylphosphine oxide, triheptylphosphine oxide, trimethylphosphine oxide, trioctylphosphine oxide, tripentylphosphine oxide, tripropylphosphine oxide, triphenylphosphine oxide, or combinations thereof.

28. The composition of claim 22 wherein the weak acid comprises boric acid, carboxylic acids, or combinations thereof.

29. The composition of claim 22 wherein the weak acid comprises acrylic acid, methacrylic acid, malonic acid, succinic acid, salicylic acid, adipic acid, maleic acid, malic acid, oleic acid, gallic acid, tartaric acid, citric acid, formic acid, acetic acid, glycolic acid, oxalic acid, tartaric acid, dextotartaric acid, mesotartaric acid, propionic acid, phthalic acid, isophthalic acid, glutaric acid, giuconic acid, lactic acid, aspartic acid, glutaminic acid, itaconic acid, trifluoroacetic acid, barbituric acid, cinnamic acid, benzoic acid, 4-hydroxybenzoic acid, aminobenzoic; a phenol, pyrogallol (benzene-1,2,3-triol), pyrocatechol (benezenediol), organoboronic acids, or combinations thereof.

30. The composition of claim 22 wherein the weak acid is characterized by an acid dissociation constant pKa value in the range of from about 2 to about 12 in water.

* * * * *